(12) United States Patent
Harrold

(10) Patent No.: US 6,508,793 B1
(45) Date of Patent: Jan. 21, 2003

(54) INVERTIBLE EYE DROP DISPENSER DEVICE

(75) Inventor: John E. Harrold, Hunterdon, NJ (US)

(73) Assignee: Valley Design, Inc., Bloomsbury, NJ (US)

( * ) Notice: Subject to any disclaimer, the term of this patent is extended or adjusted under 35 U.S.C. 154(b) by 0 days.

(21) Appl. No.: 10/007,495

(22) Filed: Nov. 5, 2001

(51) Int. Cl.[7] .............................................. A61H 33/04

(52) U.S. Cl. .................. 604/302; 604/294; 604/295

(58) Field of Search ................................ 604/294–302; 241/331

(56) References Cited

U.S. PATENT DOCUMENTS

| 3,945,381 A | 3/1976 | Silver |
| 4,834,728 A | 5/1989 | McKenna |

Primary Examiner—Dennis Ruhl
Assistant Examiner—Linh Truong
(74) Attorney, Agent, or Firm—Kenneth P. Glynn, Esq.

(57) ABSTRACT

The present invention is an invertible eye drop dispenser device, alone, and in conjunction with an eye drop dispenser container having a threaded neck. The device includes a hollow, circular base portion with a bottom end and a top end. The bottom end has a first set of internal threads and the top end has a second set of internal threads, both being of the same thread gauge, to thread onto a neck of an eye drop dispenser container. The first set of internal threads and the second set of internal threads are inverted relative to one another, so that the device may be threaded with the bottom end threaded to a container or, so that, upon inversion, the device may be threaded with the top end threaded to a container. There is also an eye cup portion attached to the bottom end of the base portion.

20 Claims, 7 Drawing Sheets

INVERTIBLE EYE DROP DISPENSER DEVICE

BACKGROUND OF THE INVENTION

1. Field of the Invention

The present invention relates to eye drop dispenser devices which are used in conjunction with eye drop dispensers and are often referred to as cups. More specifically, these devices, in general, are removably attached or permanently attached to containers (dispensers) for application of eye treatments to the human eye. The cup is especially useful in prevention of misdirection of the liquid treatment being dispensed and aids in alignment of the dispenser with the eye to be treated. In the present invention, the device is uniquely invertible and may be screwed onto a dispenser shoulder-down for compactness, and then unscrewed, inverted and screwed back onto the dispenser shoulder-up for use on an eye.

2. Information Disclosure Statement

Eye drop dispenser containers have been in use for decades and are basically squeeze containers which store eye treatment materials, such as eye medications, prescription medications, red eye treatments, dry eye treatments and the like. They are typically screwed capped, with shoulders and a tapered tip with a dispensing orifice on the neck. They are uncapped, then held upside down (inverted) and squeezed above an eye to be treated. Problems arise, such as bad aim, spillage, misdosage, and, for women, makeup damage. The present invention is directed to overcoming or reducing all of these problems. Other concepts have been developed to address some of these difficulties, but not to the extent or success of the present invention. The following patents are representative of the state of the art:

U.S. Pat. No. 4,834,728 describes a selectively securable eye drop dispenser apparatus as set forth wherein a replacement cap for use of the conventional eye drop dispensers has formed a threaded cylindrical portion for securement to the aforenoted conventional eye drop bottle including an orifice portion directed to an eye cup portion for operative associated with a human eye. The eye cup portion is formed of a flexible plastic-like material for enabling conformity to an associated human eye wherein the cylindrical threaded portion is formed of relatively stiff plastic-like material for maintaining desired registry and orientation of the associated orifice portion with the eye drop bottle.

U.S. Pat. No. 3,945,381 describes an eye drop dispenser consisting of a flexible container having an open neck defining an eye drop cup removably secured to the neck of the dispenser and having a free edge for engaging the eyelids of a person using the dispenser, in order to hold the eyelids against movement during application of eye drops to the eye. The cup is secured to the neck of the dispenser through an opening formed in one end thereof, which opening and engages the neck of the container with a portion of the neck extending through the opening and into the cup. A cover is provided for the cup and container, which cover has a top portion stem. The top portion of the cover overlies the free edge of the cup to close the open end of the cup and the elongated stem portion of the cover extends into the cup and includes means for operatively engaging and closing the neck or nozzle of the container so that the cover will simultaneously close both the dispenser nozzle and the opened end of the cup.

Notwithstanding the prior art, the present invention is neither taught nor rendered obvious thereby.

SUMMARY OF THE INVENTION

The present invention is directed to an invertible eye drop dispenser device, alone, and in conjunction with an eye drop dispenser container having a threaded neck. The device includes a hollow, circular base portion having a bottom end and a top end. The bottom end has a first set of internal threads and the top end has a second set of internal threads, the first set of internal threads and the second set of internal threads having the same thread gauge and both being adapted to thread onto threads of a neck of an eye drop dispenser container. The first set of internal threads and the second set of internal threads are inverted relative to one another, so that the device may be threaded with the bottom end threaded to a container or, so that, upon inversion, the device may be threaded with the top end threaded to a container.

There is also an eye cup portion attached to the bottom end of the base portion. The eye drop cup portion has a narrower cross section toward the base portion and flares out to a wider cross section away from the base portion. The eye cup portion may be curvilinear in shape and, in one preferred embodiment, is hemispherical in shape. Any shape may be employed for the eye cup portion as long as it is a shape adapted to nest over a shoulder area at a threaded neck of an eye drop dispenser container and further adapted for positioning around a human eye area for drop dispensing of an eye treatment.

It is a critical feature of the present invention that the base portion may be threaded to a threaded neck of an eye drop dispenser container with said the set of internal threads, and so that the eye cup portion is positioned in a nested position over the shoulders of the container for compact shipment and storage, and may subsequently be unthreaded from the container, inverted and threaded to the threads of the neck with the second set of internal threads so that the eye cup portion is oriented upwardly away from the container. In this orientation, the eye cup is ready for eye application to an eye for dispensing of treatment from the eye drop dispenser container. In the alternative to the foregoing, a user may elect to not use the invertible eye drop dispenser device and simply remove a cap and invert and dispense from the dispenser container. Thus, the user will uniquely have the choice of using the invertible eye drop dispenser device or not, to apply eye treatment.

In some embodiments of the present invention, the base portion and eye cup portion may be made as two separate pieces and assembled, e. g., threaded, heat welded or glued together. In other embodiments, the base portion and the eye cup portion are made in a single mold and are, thus, unistructural in form. Whether formed separately or unistructurally, the device is preferably made of polymeric material, but could be made of other material, such as glass, ceramic, carbon fiber or the like.

For many reasons, including safety, gentleness to the touch of the face, prevention or reduction of dripping, accuracy in dosage and absorbency the present invention device eye cup portion has an outer rim with a flexible foam pad on the outer rim. Most preferably, the flexible foam pad is at least partially open porous and is water absorbent, i.e., it is made of foam with some open foam pore structure to absorb liquid treatment material during usage.

The eye cup portion is generally curvilinear in many embodiments, and may be substantially hemiovoid substantially hemispherical in shape.

Also, in conjunction with the present invention, there is a cap for closure of the dispensing orifice of the container. In some embodiments of the present invention, the cap may be any type of cap directly attachable to the container. In other embodiments, there is an external cap attachment means located at the top end of the base for receiving a threaded cap. For example, there may be a cap with threads adapted to be threaded to external threads located on the top end of the base portion of the device. Alternatively, a cap removably connected to the top end of base portion, e.g., wherein the cap has a living hinge permanently connected to itself and to the top end of the base portion.

In yet other embodiments of the present invention, the aforesaid devices are in combination with an eye drop dispenser container having a hollow body, shoulders and a neck, the neck having cooperating threads thereon and having a dispenser orifice.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
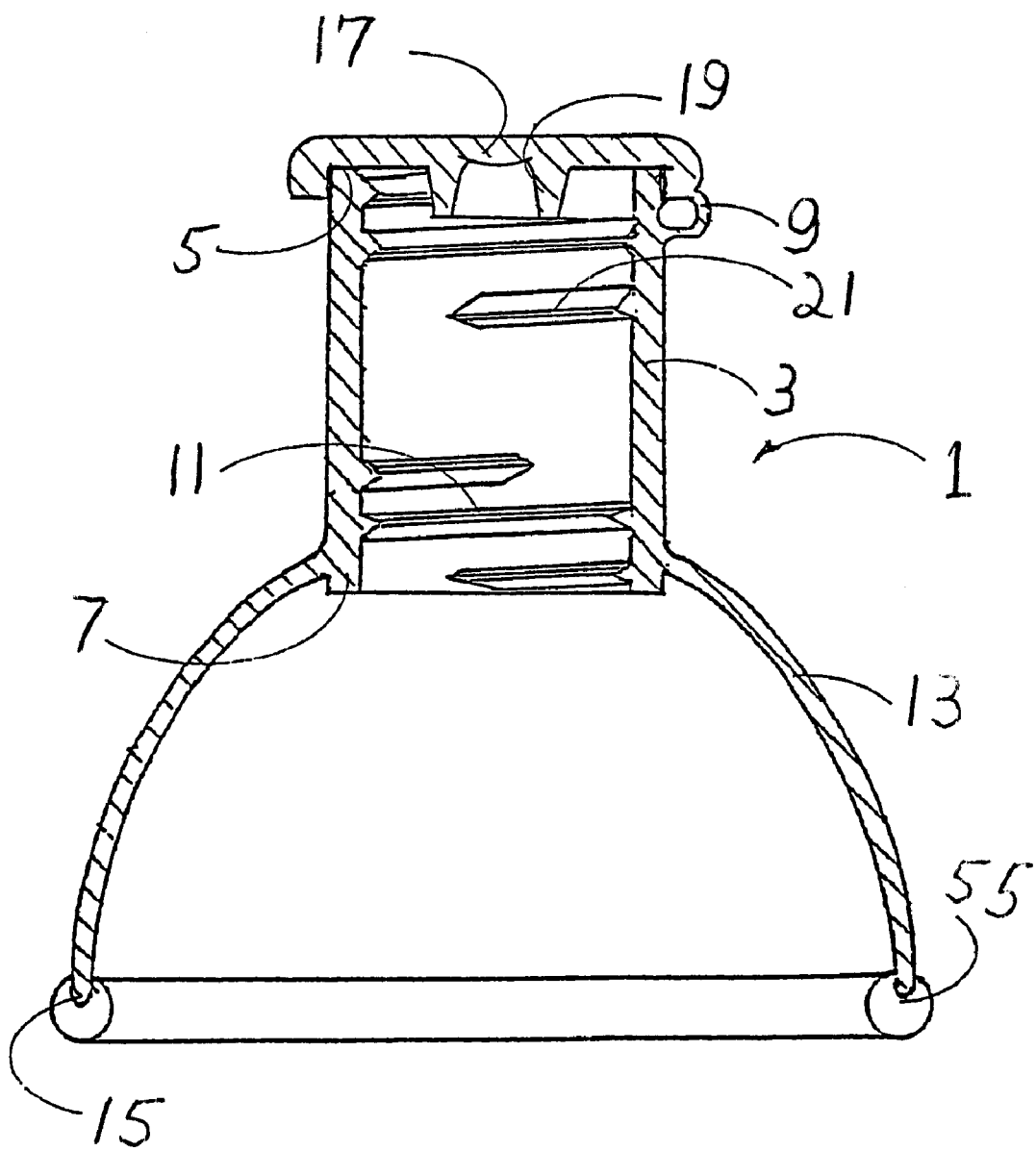
FIG. 1 illustrates a present invention device utilizing a cap which is attached to the base portion.

Referring to FIGS. 1, 2, 3 and 4, all elements that are identical are identically numbered. Present invention device 1 includes a base portion 3 and an eye cup portion 13. Base portion 3 has a top end 5 and a bottom end 7. Each end has a set of internal threads 11 and 21, respectively, which have the same gauge (pitch and threads per inch), so that both can be screwed onto the same threads, but are inverted relative to one another. In this embodiment, there is a cap 17, which could be any type of cap, for attachment to the top end 5 of base portion 3. Here, cap 17 is permanently attached via living hinge 9 (a flexible plastic strand) to base portion 3, and is adapted for attachment to top end 5 as a simple snap cap (frictionally fitted to close tightly). In addition, it is designed internally to seal a dispensing orifice with seal annulus 19.

Eye cup portion 13 includes an outer rim 15, and, in this embodiment, contains a foam pad 55. This pad 55 is made of partially open pore foam. It functions to cushion the device when held to the face, and it functions to prevent spillage, as it is liquid absorbent. These features are important to the comfort and sometimes the safety of the user, and aide to assure dosages are more accurate to the eye, to prevent waste and to avoid undesirable contact, e.g., to the nose, mouth, makeup on the face, to clothing, etc.

Figure 2:
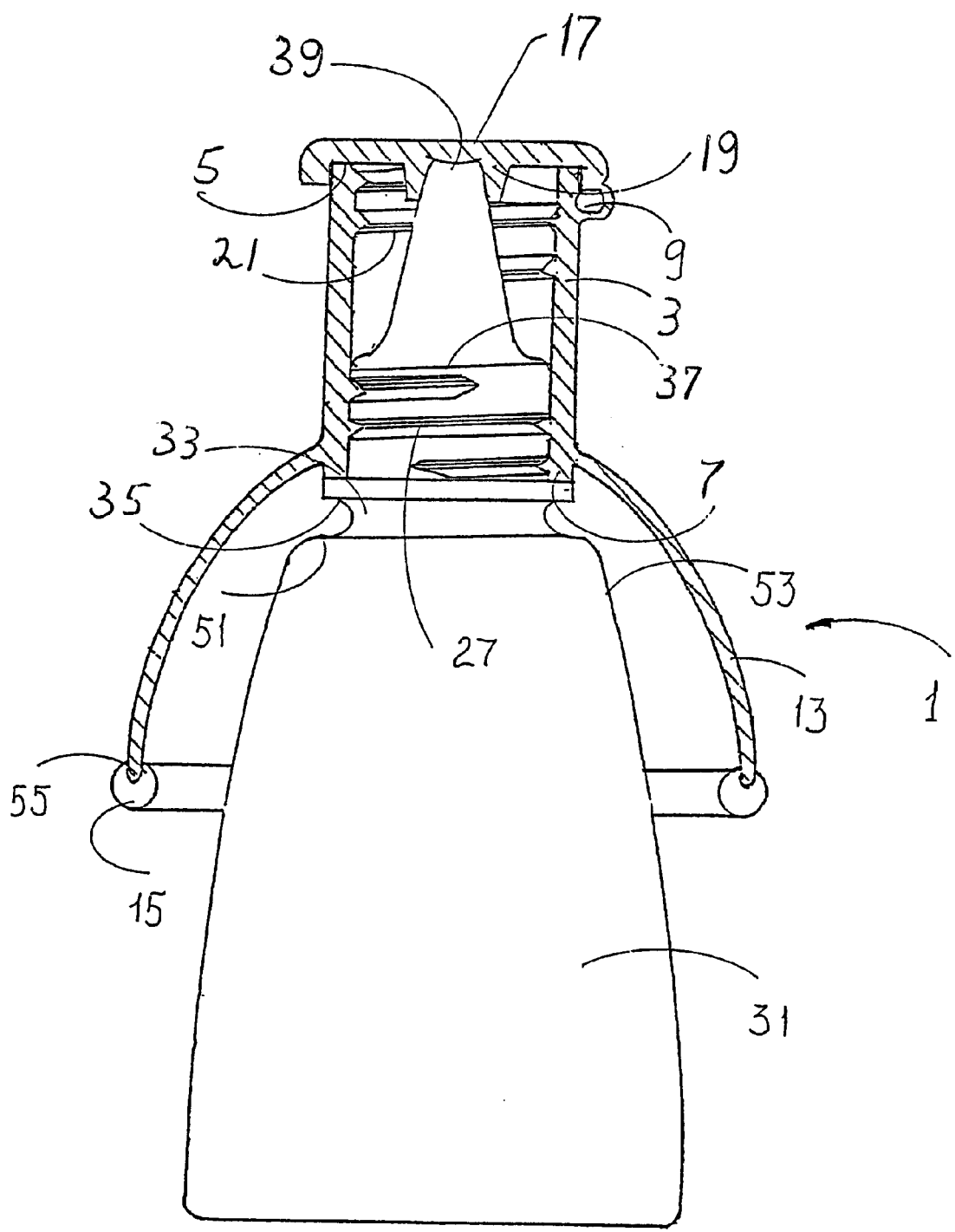
FIG. 2 shows that device attached to a container in its storage orientation.
Figure 3:
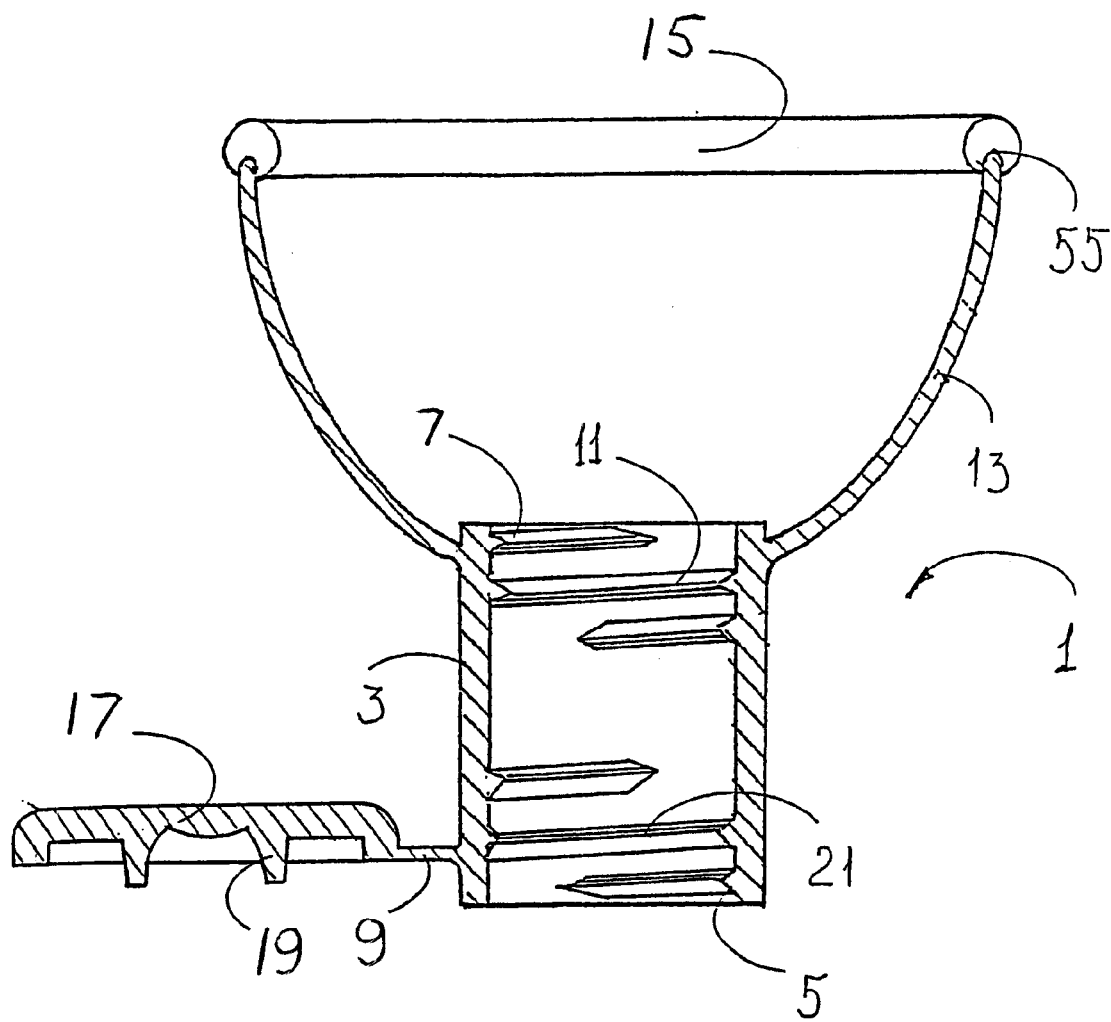
FIG. 3 shows it inverted with the cap open.

FIG. 1 shows device 1 upright with the cap closed, and FIG. 3 shows it inverted with the cap open. FIG. 2 illustrates the device as shown in FIG. 1, but positioned in a closed position on eye drop dispenser container 31. Container 31 is a typical eye drop dispenser container with liquid (typically water-based) treatment contained therein, and includes shoulders 51 and 53, neck 37 with threads (grooves) 27 and flange 35. Note that bottom end 7 of device 1 stops at and sits on flange 35 as it is threaded onto container neck 37, and that eye cup portion 13 nests on shoulders 51 and 53. (Nesting is used to suggest fitting over and may or may not be a snug or contacting fit.) Also, cap 17 is fitted by seal annulus 19 onto dispensing orifice 39, as shown.

Figure 4:
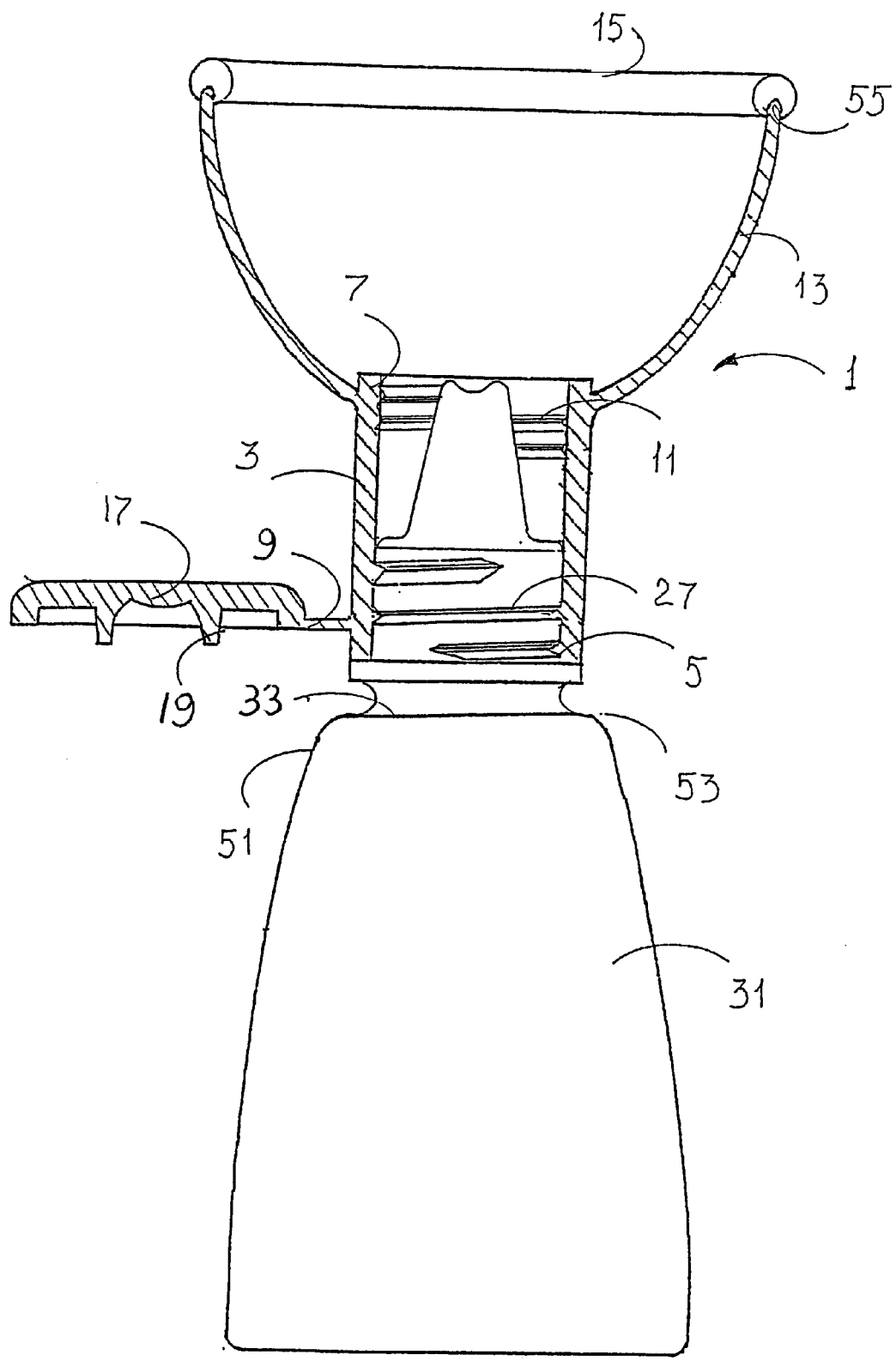
FIG. 4 shows it on the container in its open cap, inverted orientation for eye application use.

Referring to FIG. 4, the device 1 as shown in its inverted orientation in FIG. 3 is repeated, but is now positioned in its dispensing orientation on container 31, again, with all identical elements of FIGS. 1 through 4 identically numbered.

Figure 5:
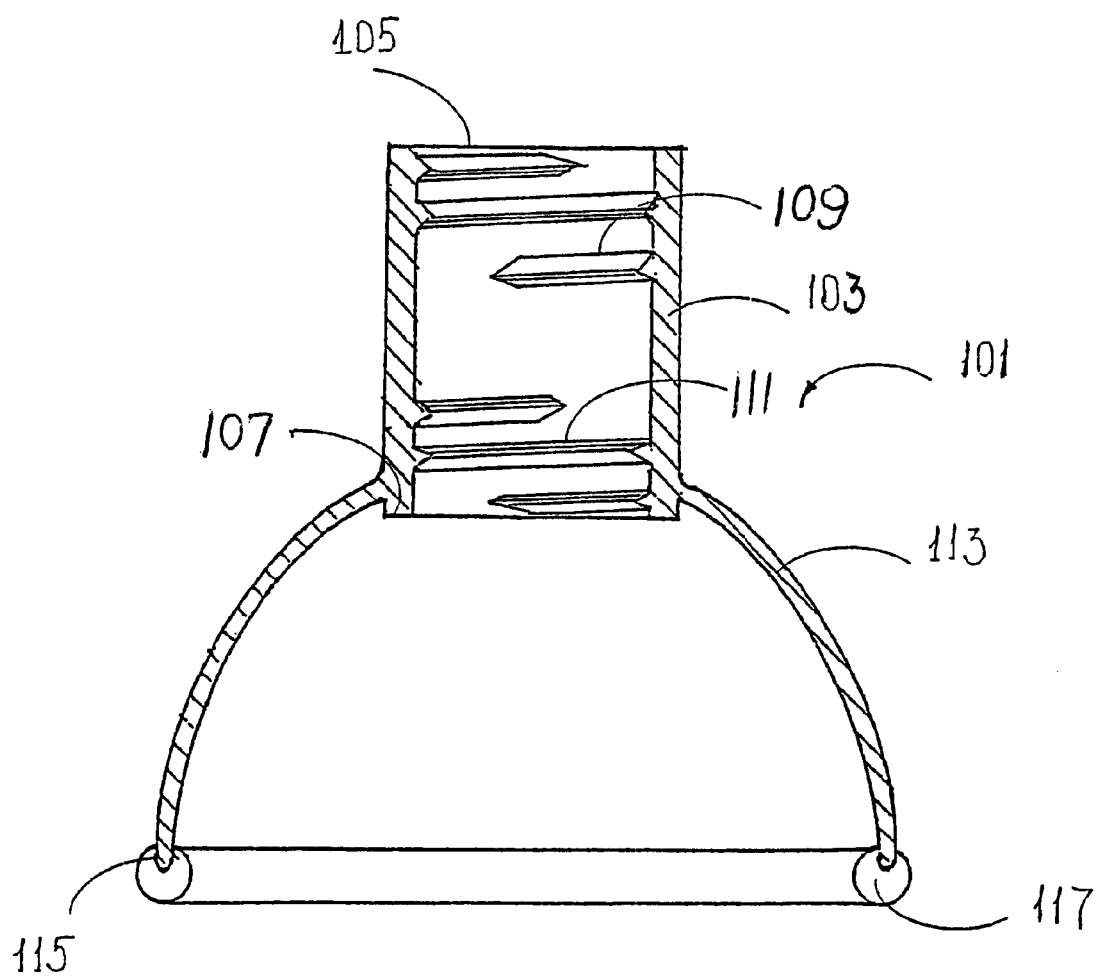
FIG. 5 shows an alternative present invention device with no cap or cap attachment, and FIG. 6 illustrate that device on a container which has a separate cap; and, FIG. 7 illustrates an embodiment wherein the cap is screwed onto the device and is fully removable therefrom.
Figure 6:
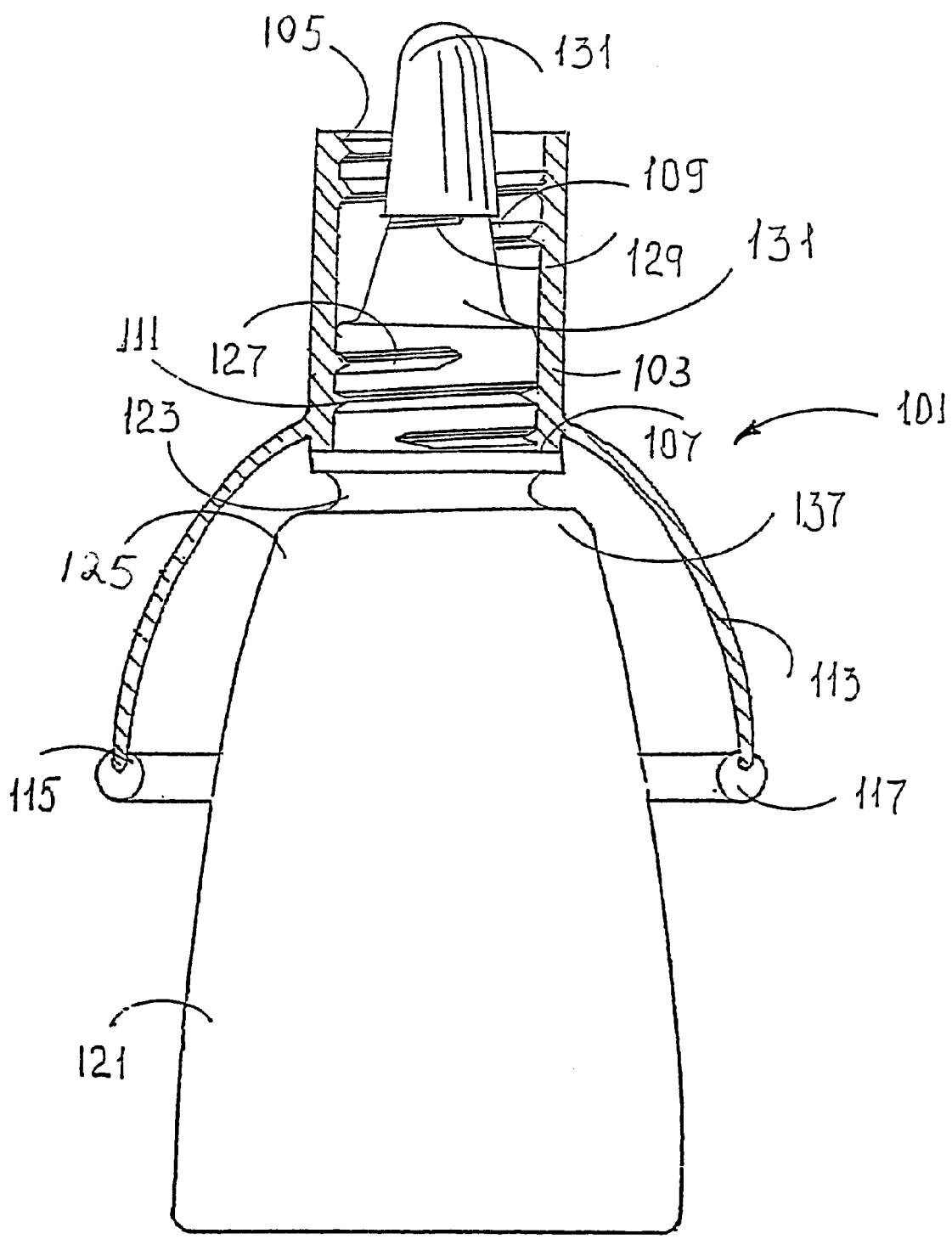

FIGS. 5 and 6 show another present invention embodiment with no cap. Here, device 101 includes a base portion 103 and an eye cup portion 113. Base portion 103 has a top end 105 and a bottom end 107. Each end has a set of internal threads 109 and 111, respectively, which have the same gauge and are inverted relative to one another. Eye cup portion 113 includes an outer rim 115, and, in this embodiment, contains a foam pad 117, which is made of partially open pore foam. It functions to cushion the device when held to the face, and to prevent spillage during use. In FIG. 6, it is shown in place on eye drop dispenser container 121.

Container 121 is an eye drop dispenser container with liquid treatment contained therein, and includes shoulders 125 and 137, neck 131 with threads (grooves) 127 and flange 123. Bottom end 107 of device 101 stops at and rests on flange 123, as shown. Eye cup portion 113 nests on shoulders 125 and 137. In this embodiment, container 121 has a threaded neck 131 with threads 129, which has its own cap 131, which is independent of device 101. Thus, it becomes unnecessary to attach a cap or include a cap with the device 101 itself. In use, device 101 is removed from the container 121, then neck cap 131 is removed, device 101 is inverted and rethreaded to the container 121 and then the assemblage is placed over an eye to be treated and the container is squeezed to dispense the treatment.

Figure 7:
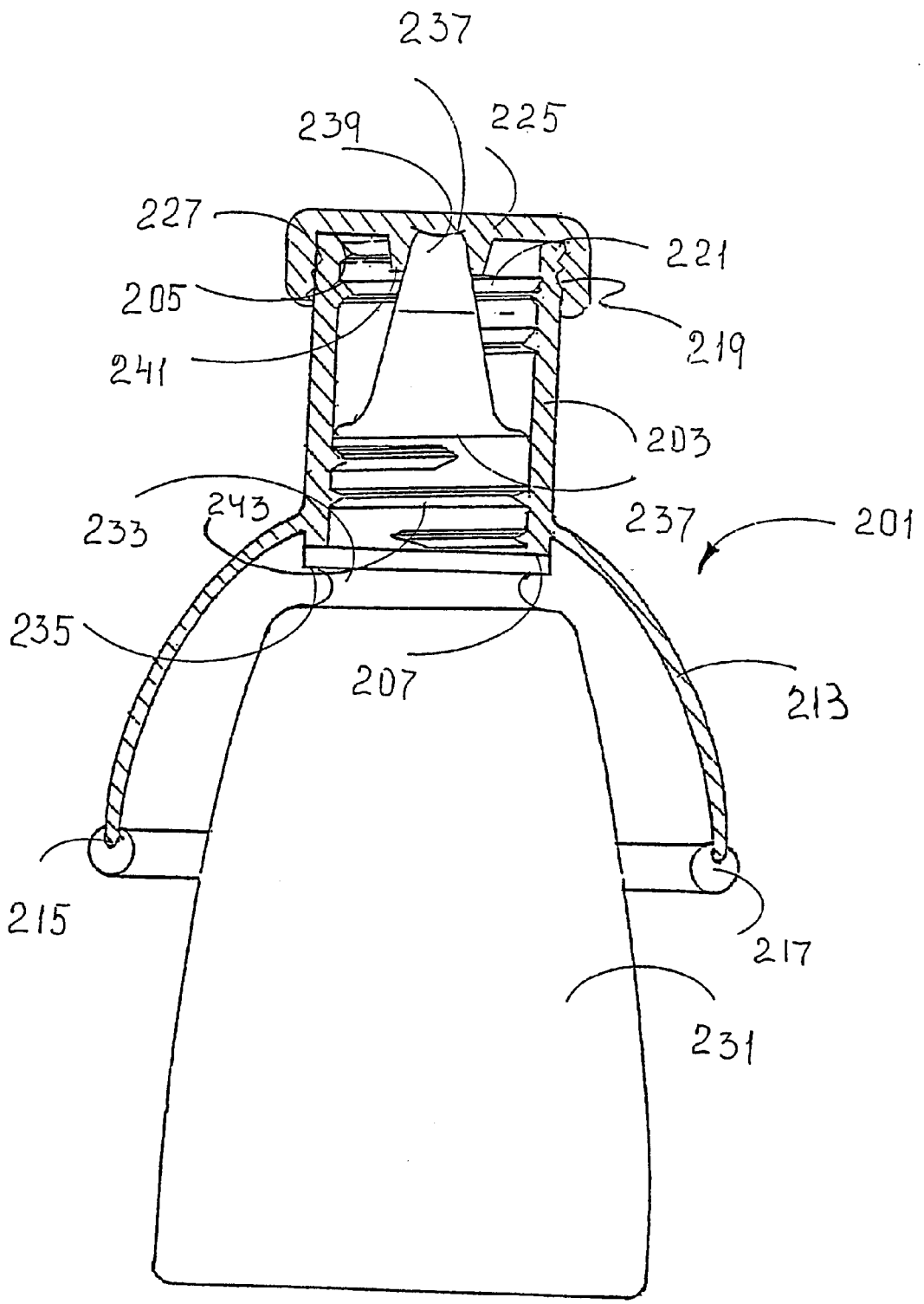

FIG. 7 shows another embodiment present invention embodiment with an unattached cap for the device. In FIG. 7, device 201 includes a base portion 203 and an eye cup portion 213. Base portion 203 has a top end 205 and a bottom end 207. Each end has a set of internal threads, such as threads 221, having the same gauge and are inverted relative to one another. Eye cup portion 213 includes an outer rim 215, and, in this embodiment, contains a foam pad 217, which is made of partially open pore foam. It functions to cushion the device when held to the face, and to prevent spillage during use. Device 301 is shown in place on eye drop dispenser container 231. Neck 237 with threads (grooves) 243 and flange 223. Bottom end 207 of device 201 stops at and rests on flange 233, as shown. Eye cup portion 113 nests over the shoulders of container 231 an. In this embodiment, cap 225, which is removably connected to top end 205 of device 201, includes inside threads 227 on cap 225, and corresponding external threads 219 on the outside of top end 205 of device 201. Except for the fact that cap 225 is fully removable, this assemblage works in the same manner as the present invention device 101 described above.

Obviously, numerous modifications and variations of the present invention are possible in light of the above teachings. It is therefore understood that within the scope of the appended claims, the invention may be practiced otherwise than as specifically described herein.

What is claimed is:

1. An invertible eye drop dispenser device for use with an eye drop dispenser container having a threaded neck, which comprises:
    (a) a hollow, circular base portion having a bottom end and a top end, said bottom end having a first set of internal threads and said top end having a second set of internal threads, said first set of internal threads and said second set of internal threads having the same thread gauge and both being adapted to thread onto a same threaded neck of an eye drop dispenser container, said first set of internal threads and said second set of internal threads being inverted relative to one another; and,
    (b) an eye cup portion attached to said bottom end of said base portion, said eye drop cup portion having a narrower cross section toward said base portion and a wider cross section away from said base portion, said eye cup portion having a shape adapted to nest over a shoulder area at a threaded neck of an eye drop dispenser container and further adapted for positioning around a human eye area for drop dispensing of an eye treatment;
    (c) wherein said base portion may be threaded to a threaded neck of an eye drop dispenser container with said first set of internal threads and with said eye cup portion positioned in a nested position over a shoulder area of said container for compact shipment and storage, and may subsequently be unthreaded from said container, inverted and threaded to said threaded neck with said second set of internal threads with said eye cup portion oriented upwardly away from said container and ready for eye application for dispensing of treatment from said eye drop dispenser container.

2. The device of claim 1 wherein said base portion and said eye cup portion are unistructural in form and are made of polymeric material.

3. The device of claim 1 wherein said eye cup portion has an outer rim and there is a flexible foam pad on said outer rim.

4. The device of claim 3 wherein said flexible foam pad is at least partially open porous and is water absorbent.

5. The device of claim 1 wherein said eye cup portion is curvilinear in shape.

6. The device of claim 1 wherein said eye cup portion is substantially hemispherical in shape.

7. The device of claim 1 wherein said device further includes external cap attachment means located at said top end of said base for receiving a threaded cap.

8. The device of claim 7 wherein said device further includes a cap with threads adapted to be threaded to said external threads.

9. The device of claim 1 wherein said device includes a cap removably connected to said top end of said base portion.

10. The device of claim 9 wherein said cap has a living hinge permanently connected to said top end of said base portion.

11. An invertible eye drop dispenser device and eye drop dispenser container having a threaded neck, which comprises:
    (a) an eye drop dispenser container having a hollow body, shoulders and a neck, said neck having threads thereon and having a dispenser orifice;
    (b) a hollow, circular base portion having a bottom end and a top end, said bottom end having a first set of internal threads and said top end having a second set of internal threads, said first set of internal threads and said second set of internal threads having the same thread gauge and both being adapted to thread onto said threads of said neck of said eye drop dispenser container, said first set of internal threads and said second set of internal threads being inverted relative to one another; and,
    (c) an eye cup portion attached to said bottom end of said base portion, said eye drop cup portion having a narrower cross section toward said base portion and a wider cross section away from said base portion, said eye cup portion having a shape adapted to nest over a shoulder area at a threaded neck of an eye drop dispenser container and further adapted for positioning around a human eye area for drop dispensing of an eye treatment;
    (d) wherein said base portion may be threaded to said threaded neck of said eye drop dispenser container with said first set of internal threads and with said eye cup portion positioned in a nested position over said shoulders of said container for compact shipment and storage, and may subsequently be unthreaded from said container, inverted and threaded to said threads of said neck with said second set of internal threads with said eye cup portion oriented upwardly away from said container and ready for eye application for dispensing of treatment from said eye drop dispenser container.

12. The device of claim 11 wherein said base portion and said eye cup portion are unistructural in form and are made of polymeric material.

13. The device of claim 11 wherein said eye cup portion has an outer rim and there is a flexible foam pad on said outer rim.

14. The device of claim 13 wherein said flexible foam pad is at least partially open porous and is water absorbent.

15. The device of claim 11 wherein said eye cup portion is curvilinear in shape.

16. The device of claim 11 wherein said eye cup portion is substantially hemispherical in shape.

17. The device of claim 11 wherein said device further includes external cap attachment means located at said top end of said base for receiving a threaded cap.

18. The device of claim 17 wherein said device further includes a cap with threads adapted to be threaded to said external threads.

19. The device of claim 11 wherein said device includes a cap removably connected to said top end of said base portion.

20. The device of claim 19 wherein said cap has a living hinge permanently connected to said top end of said base portion.

* * * * *